(12) United States Patent
Bloomquist et al.

(10) Patent No.: US 12,138,163 B2
(45) Date of Patent: Nov. 12, 2024

(54) FULLY DEPLOYABLE AND RECAPTURABLE PROSTHETIC HEART VALVE

(71) Applicant: St. Jude Medical, Cardiology Division, Inc., St. Paul, MN (US)

(72) Inventors: Alex L. Bloomquist, Mound, MN (US); Kristopher Henry Vietmeier, Monticello, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 281 days.

(21) Appl. No.: 17/142,561

(22) Filed: Jan. 6, 2021

(65) Prior Publication Data

US 2021/0205080 A1 Jul. 8, 2021

Related U.S. Application Data

(60) Provisional application No. 62/958,456, filed on Jan. 8, 2020.

(51) Int. Cl.
*A61F 2/24* (2006.01)

(52) U.S. Cl.
CPC .......... *A61F 2/2439* (2013.01); *A61F 2/2418* (2013.01); *A61F 2/2436* (2013.01); *A61F 2220/0075* (2013.01); *A61F 2250/001* (2013.01); *A61F 2250/0012* (2013.01)

(58) Field of Classification Search
CPC .... A61F 2/2418; A61F 2/2436; A61F 2/2439; A61F 2002/9511; A61F 2/2427
See application file for complete search history.

(56) References Cited

U.S. PATENT DOCUMENTS

| | | |
|---|---|---|
| 9,039,759 B2 | 5/2015 | Alkhatib et al. |
| 9,180,004 B2 | 11/2015 | Alkhatib |
| 9,545,309 B2 | 1/2017 | Alkhatib et al. |
| 9,775,707 B2 | 10/2017 | Alkhatib et al. |
| 2005/0033398 A1 | 2/2005 | Seguin |
| 2005/0137697 A1 | 6/2005 | Salahieh et al. |
| 2006/0259136 A1 | 11/2006 | Nguyen et al. |
| 2007/0244552 A1 | 10/2007 | Salahieh et al. |
| 2009/0192585 A1 | 7/2009 | Bloom et al. |
| 2010/0049313 A1 | 2/2010 | Alon et al. |
| 2017/0156859 A1* | 6/2017 | Chang ............... A61F 2/2439 |
| 2017/0209268 A1* | 7/2017 | Cunningham ........ A61F 2/95 |

* cited by examiner

*Primary Examiner* — Suba Ganesan
(74) *Attorney, Agent, or Firm* — SLEMAN & LUND LLP

(57) ABSTRACT

A heart prosthesis system may include a prosthetic heart valve and a length of suture. The prosthetic heart valve may include a collapsible and expandable stent and a valve assembly mounted within the stent. The stent may have an aortic end, an annulus end, and a plurality of openings arranged circumferentially around the aortic end, the aortic end having a first diameter in an expanded condition. The length of suture may be threaded through the openings such that tension applied to the length of suture in a direction away from the stent may collapse the aortic end of the stent from the first diameter to a second diameter less than the first diameter.

8 Claims, 9 Drawing Sheets

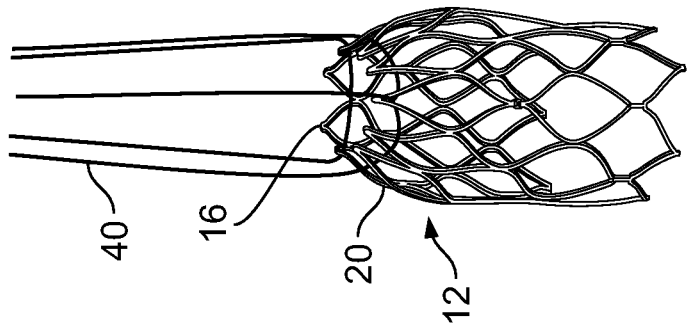
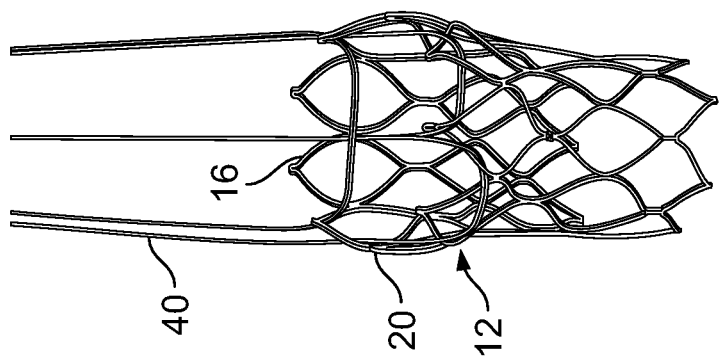
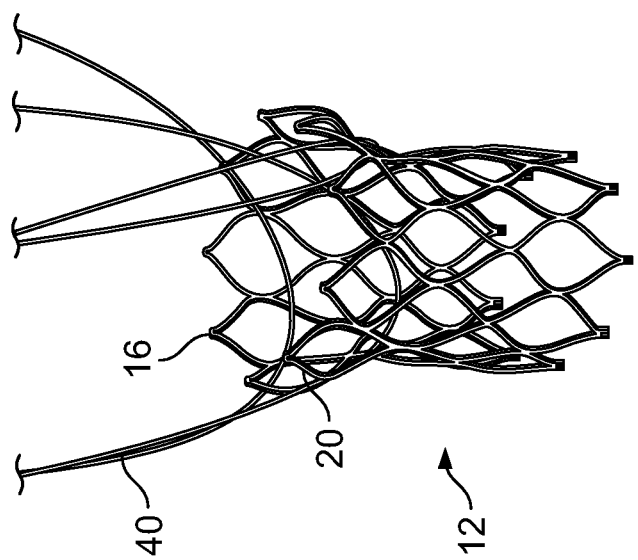

FULLY DEPLOYABLE AND RECAPTURABLE PROSTHETIC HEART VALVE

CROSS-REFERENCE TO RELATED APPLICATIONS

The present application claims the benefit of the filing date of U.S. Provisional Patent Application No. 62/958,456 filed Jan. 8, 2020, the disclosure of which is hereby incorporated by reference.

BACKGROUND

The present invention relates to collapsible prosthetic heart valve implantation, and more particularly, to apparatus and methods for ensuring proper positioning and stabilization of the prosthetic heart valve during implantation.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed to reduce its circumferential size.

When a collapsed prosthetic valve has reached the desired implantation site in the patient (e.g., at or near the annulus of the patient's heart valve that is to be repaired by the prosthetic valve), the prosthetic valve can be deployed or released from the delivery apparatus and expanded to its full operating size. For balloon-expandable valves, this generally involves releasing the entire valve, assuring its proper location, and then expanding a balloon positioned within the valve stent. For self-expanding valves, on the other hand, the stent automatically expands as the stent is withdrawn from the delivery apparatus.

The clinical success of collapsible heart valves is dependent, in part, on the accurate positioning of the valve within the native valve annulus. Inaccurate placement and/or anchoring of the valve may result in the leakage of blood between the prosthetic heart valve and the native valve annulus. This phenomenon is commonly referred to as paravalvular leakage. In aortic valves, paravalvular leakage enables blood to flow from the aorta back into the left ventricle during systole, resulting in reduced cardiac efficiency and strain on the heart muscle.

Despite the various improvements that have been made to transcatheter aortic valve repair devices, conventional delivery devices suffer from various shortcomings. For example, in conventional delivery devices, it may be difficult to correctly position the delivery device at or near the native annulus of the patient and to simultaneously deploy the prosthetic heart valve. Moreover, full deployment of the heart valve sometimes causes the valve to "jump" or reposition when the aortic end of the stent engages with tissue. In those instances, when the valve has been improperly deployed or has moved to an improper position after being fully deployed, the prosthetic heart valve would need to be entirely removed from the patient. Removing a fully deployed prosthetic heart valve requires invasive surgery and greatly increases the risk to the patient.

Therefore, there is a need for further improvements to the systems and methods for transcatheter delivery of collapsible prosthetic heart valves, and in particular, self-expanding prosthetic heart valves.

BRIEF SUMMARY

A heart prosthesis system may include a prosthetic heart valve and a length of suture. The prosthetic heart valve may include a collapsible and expandable stent and a valve assembly mounted within the stent. The stent may have an aortic end, an annulus end, and a plurality of openings arranged circumferentially around the aortic end, the aortic end having a first diameter in an expanded condition. The length of suture may be threaded through the openings such that tension applied to the length of suture in a direction away from the stent may collapse the aortic end of the stent from the first diameter to a second diameter less than the first diameter.

BRIEF DESCRIPTION OF THE DRAWINGS

Various embodiments of the present invention are described herein with reference to the drawings, wherein:

FIGS. 9A-9C are illustrations of the collapsible prosthetic heart valve of FIG. 1 in progressive stages of constriction by sutures.

DETAILED DESCRIPTION

As used herein in connection with a prosthetic heart valve, the term "inflow end" refers to the end of the heart valve through which blood enters when the heart valve is functioning as intended, and the term "outflow end" refers to the end of the heart valve through which blood exits when the heart valve is functioning as intended. As used herein in connection with a prosthetic heart valve, the term "proximal" refers to the inflow end of the heart valve or to elements of the heart valve that are relatively close to the inflow end, and the term "distal" refers to the outflow end of the heart valve or to elements of the heart valve that are relatively close to the outflow end. When used in connection with devices for delivering a prosthetic heart valve into a patient, the terms "proximal" and "distal" are to be taken as relative to the user of the delivery devices. "Proximal" is to be understood as relatively close to the operator, and "distal" is to be understood as relatively farther away from the operator. As used herein, the terms "substantially," "generally," "approximately," and "about" are intended to mean that slight deviations from absolute are included within the scope of the term so modified. Although the various features of the prosthetic heart valve recited herein are described in connection with a valve for replacing the function of a native aortic valve, it will be appreciated that these features may also be applied to valves for replacing the function of other cardiac valves, including the mitral valve, tricuspid valve and pulmonary valve.

Figure 1:
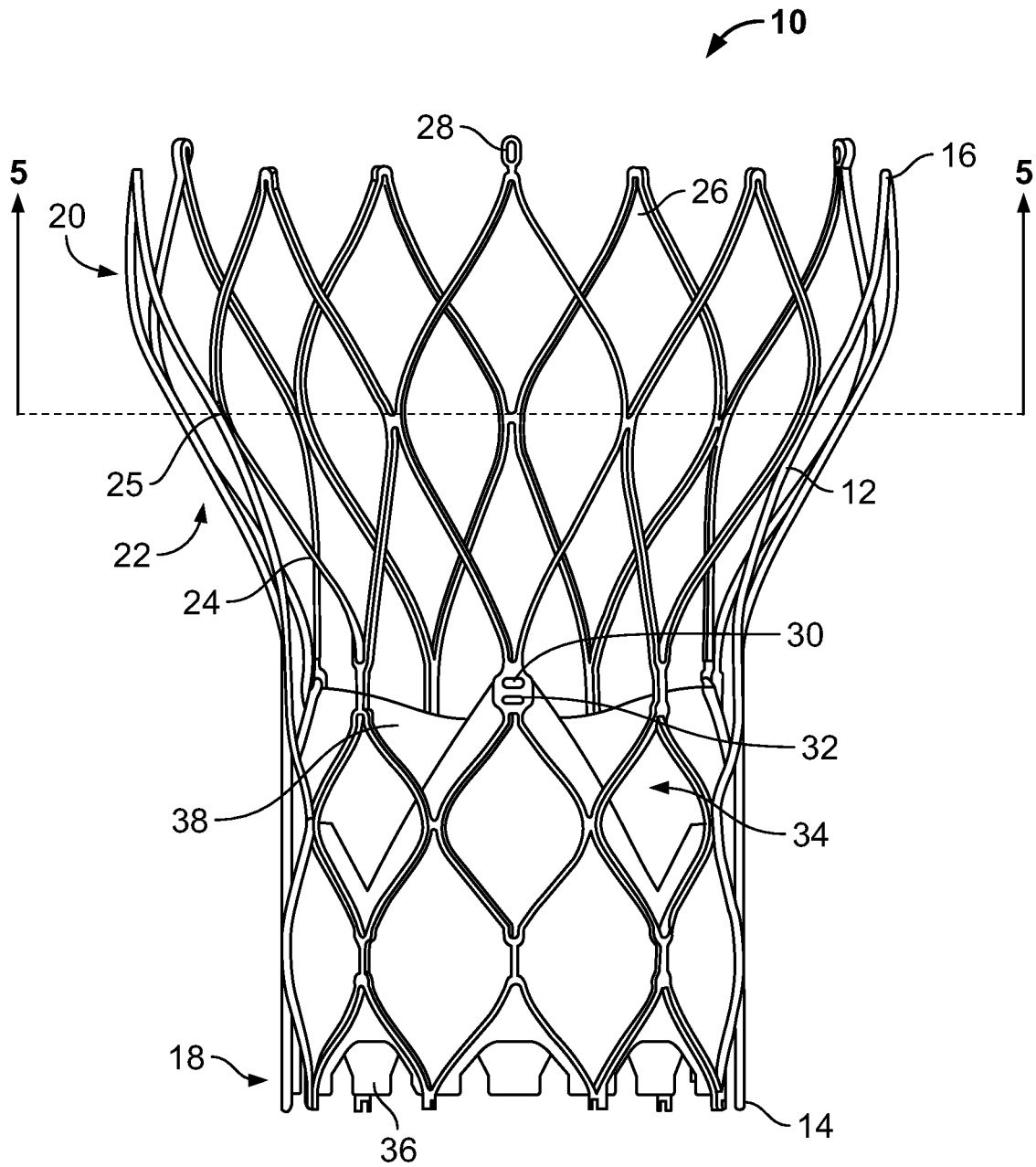
FIG. 1 is a side elevational view of a prosthetic heart valve in accordance with the prior art.

FIG. 1 illustrates a collapsible prosthetic heart valve 10 that is designed to replace the function of the native aortic valve of a patient. Prosthetic heart valve 10 includes an expandable stent 12 which may be formed from biocompatible materials that are capable of self-expansion, for example, shape memory alloys such as nitinol. Heart valve 10 extends from an inflow or annulus end 14 to an outflow or aortic end 16, and includes an annulus section 18 adjacent the inflow end and an aortic section 20 adjacent the outflow end. Annulus section 18 has a relatively small cross-section in an expanded condition compared to aortic section 20 in the expanded condition. Annulus section 18 may be in the form of a cylinder having a substantially constant diameter along its length. A transition section 22 tapers outwardly from annulus section 18 to aortic section 20. Stent 12 includes a plurality of struts 24 which form a plurality of cells 26 that are connected to one another in one or more annular rows around the stent. Stent 12 in annulus section 18 may have two annular rows of complete cells 26 and the aortic section 20 and transition section 22 of the stent may each have one or more annular rows of complete or partial cells. The cells in aortic section 20 may be larger than the cells in annulus section 18. A row of cells 26 at the aortic end 16 abut each other circumferentially within a plane in which section line 5-5 extends, where pairs of struts 24 meet each other at junctures 25. Each reference to a juncture 25 herein shall be understood to refer to a position at which two pairs of circumferentially adjacent struts 24 join or abut one another. The larger cells in aortic section 20 facilitate positioning prosthetic valve 10 within the native aortic annulus such that stent 12 does not interfere with blood flow to the coronary arteries.

Stent 12 includes one or more retaining elements 28 at outflow end 16. Retaining elements 28 are sized to cooperate with a corresponding retaining structure on a delivery device for prosthetic heart valve 10. This cooperation minimizes axial movement of the prosthetic heart valve relative to the delivery device during unsheathing or resheathing procedures, and prevents rotation of the prosthetic heart valve relative to the delivery device as the delivery device is advanced to the target location and during deployment.

Stent 12 may also include a plurality of commissure attachment features 30 for attaching the commissure between two adjacent valve leaflets (described below) to the stent. As shown in FIG. 1, commissure attachment features 30 may lie at the intersection of four cells 26, two of the cells being adjacent to one another in the same annular row, and the other two cells being in different annular rows and lying in an end-to-end relationship. Commissure attachment features 30 are preferably positioned entirely within annulus section 18, or at the juncture of the annulus section and transition section 22. Commissure attachment features 30 may include one or more eyelets 32 which facilitate the suturing of the leaflet commissure to stent 12.

Prosthetic heart valve 10 also includes a valve assembly 34, which may be positioned entirely within annulus section 18 and secured to stent 12 by suturing the valve assembly to struts 24 and/or to commissure attachment features 30. That is, the entire valve assembly 34 is axially positioned between the inflow end 14 of stent 12 and commissure attachment features 30, such that none of the valve assembly is positioned between the commissure attachment features and the outflow end 16 of the stent. Valve assembly 34 includes a cuff 36 and a plurality of leaflets 38 that open and close collectively to function as a one-way valve. Since FIG. 1 illustrates a prosthetic heart valve for replacing a native tricuspid valve, such as the aortic valve, valve 10 is illustrated with three leaflets 38, as well as three commissure attachment features 30. However, it will be appreciated that prosthetic heart valves may have a greater or lesser number of leaflets 38 and/or commissure attachment features 30. Both cuff 36 and leaflets 38 may be wholly or partly formed of any suitable biological material, such as bovine or porcine pericardium, or biocompatible polymers, such as PTFE, urethanes and the like.

Prosthetic heart valve 10 may be delivered to the desired site (e.g., at or near the native aortic annulus) using any suitable delivery device, such as a known catheter delivery system. The delivery device may be introduced into the patient using a transfemoral, transapical or transseptal approach, or another approach. Once prosthetic heart valve 10 is properly positioned inside the native aortic annulus of the patient, it works as a one-way valve, allowing blood to flow from the left ventricle to the aorta, and preventing blood from returning from the aorta to the left ventricle.

Figure 2:
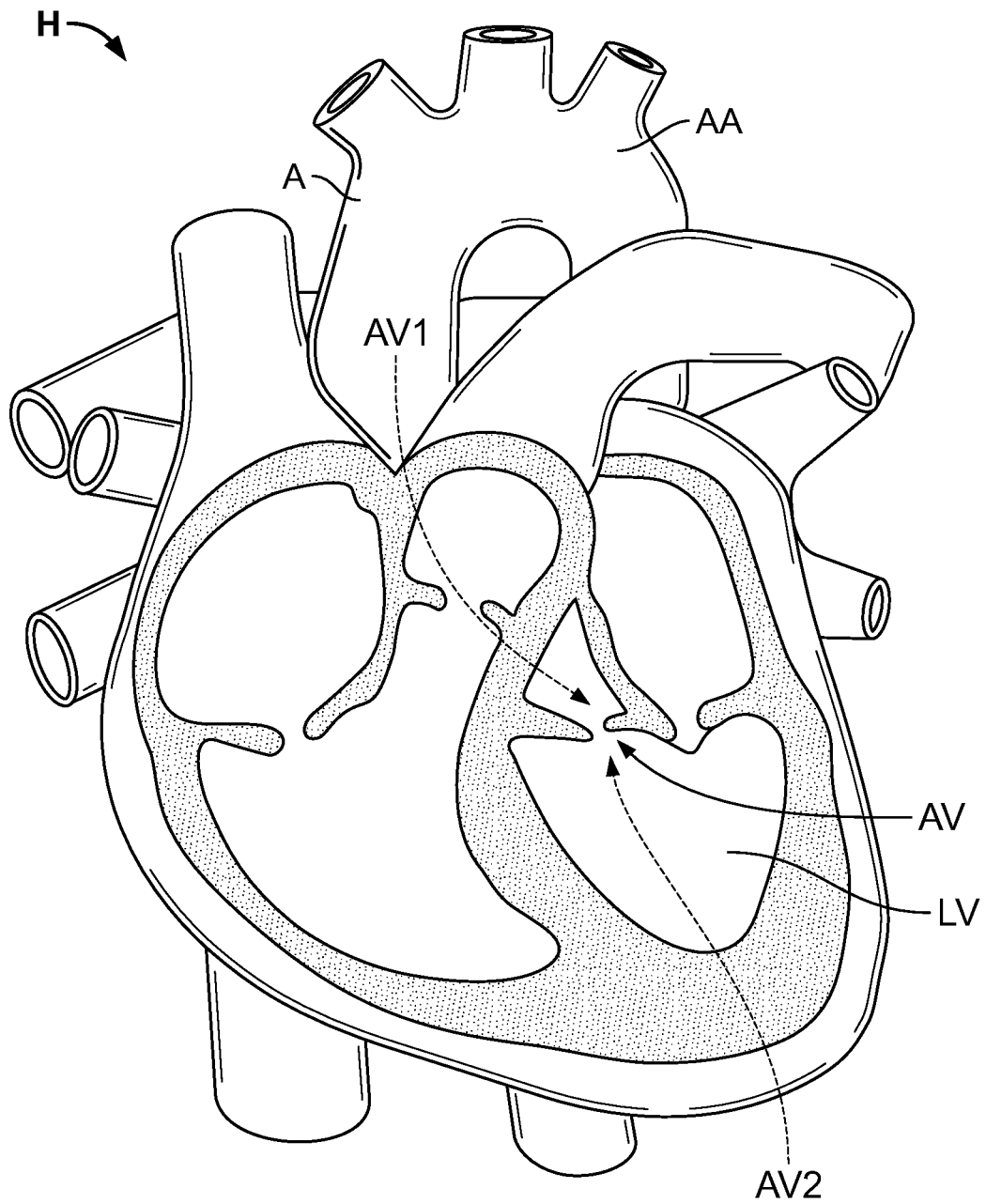
FIG. 2 is a highly schematic cutaway view of the human heart, showing two approaches for delivering a prosthetic aortic heart valve.

FIG. 2 illustrates a human heart H and two different approaches for delivering prosthetic heart valve 10 to its intended target at the aortic valve AV. As illustrated in FIG. 2, heart H includes aorta A, aortic arch AA and left ventricle LV. Two separate paths are shown for introducing prosthetic heart valve 10 to the aortic valve AV. A transfemoral approach for delivering the prosthetic heart valve is indicated by the dashed arrow labeled "AV1". In this method, prosthetic heart valve 10 is inserted into the femoral artery, tracked through the vasculature and then introduced to the target site via aortic arch AA. Echocardiography and other means may be used to help guide the delivery device through this approach. A second dashed arrow, labeled "AV2," indicates a transapical approach for delivering the prosthetic heart valve. In transapical delivery, a small incision is made between the ribs and into the apex of left ventricle LV to deliver the prosthetic heart valve to the target site.

Figure 3:
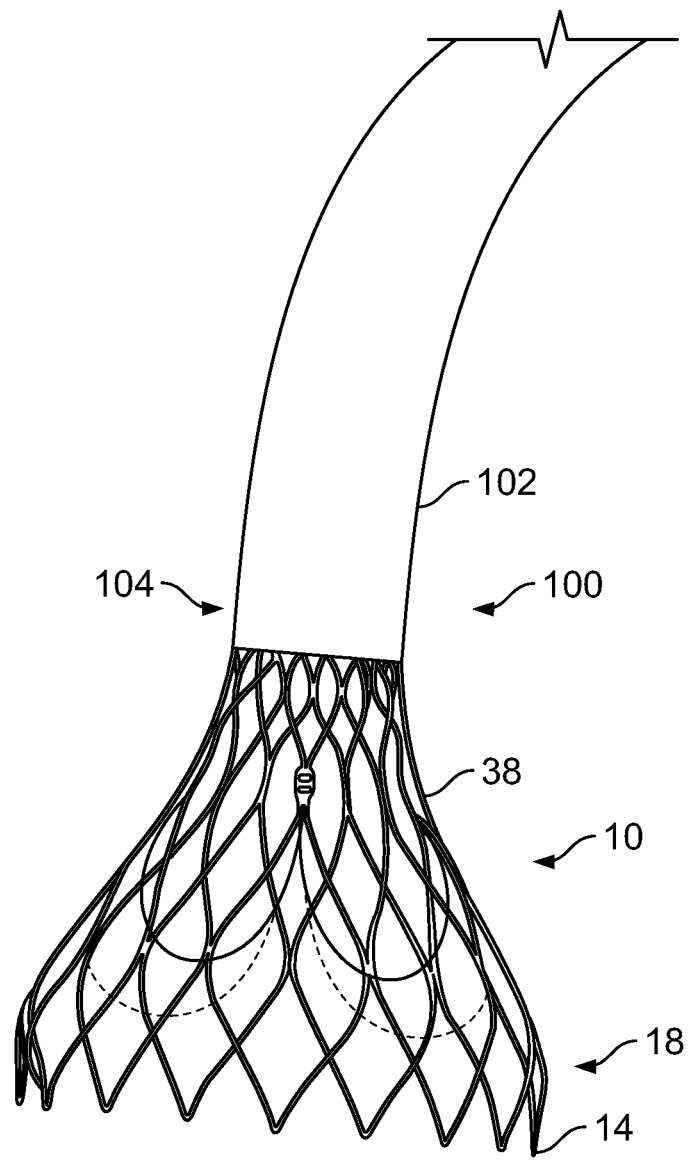
FIG. 3 is a highly schematic fragmentary view showing the partial deployment of a collapsible prosthetic heart valve from a conventional delivery device using a trans femoral approach.

FIG. 3 illustrates prosthetic heart valve 10 being delivered to the aortic valve AV of a patient within a conventional delivery device 100 using a transfemoral approach. During advancement, prosthetic heart valve 10 is disposed in a compartment within delivery device 100 and held in a collapsed configuration by distal sheath 102, with annulus section 18 closest to the distal or leading end 104 of the distal sheath. In the transfemoral approach, the annulus section 18 of prosthetic heart valve 10 is unsheathed first, thus allowing the annulus section to expand prior to full deployment of the valve. For example, distal sheath 102 may be retracted proximally, toward the user, while internal components (not shown) of delivery device 100 hold prosthetic heart valve 10 stationary. The aortic section 20 of valve 10 remains at least partially covered and constrained by distal sheath 102, while the annulus section 18 of the valve fully expands. In this manner, the position of prosthetic heart valve 10 can be evaluated and the function of leaflets 38 may be tested without fully deploying the prosthetic heart valve. Unlike the transapical approach in which prosthetic heart valve 10 is delivered through the apex of left ventricle LV and along a generally linear path to aortic valve AV, the transfemoral approach requires that the delivery device be bent through the aortic arch AA. As seen in FIG. 3, due to the anatomical curvature of aortic arch AA, it is more difficult to properly align distal sheath 102, and in turn prosthetic heart valve 10, within the annulus of the native aortic valve using a transfemoral approach than it is to align the prosthetic valve within the native aortic annulus using a transapical approach.

Even if a surgeon is able to properly navigate aortic arch AA and align prosthetic heart valve 10 within the aortic annulus prior to its deployment, self-expanding prosthetic valves are subject to "jump" and become repositioned when the aortic section 20 of the valve engages tissue. Such repositioning may occur irrespective of whether a transfemoral, transapical or other approach is used.

Figure 4:
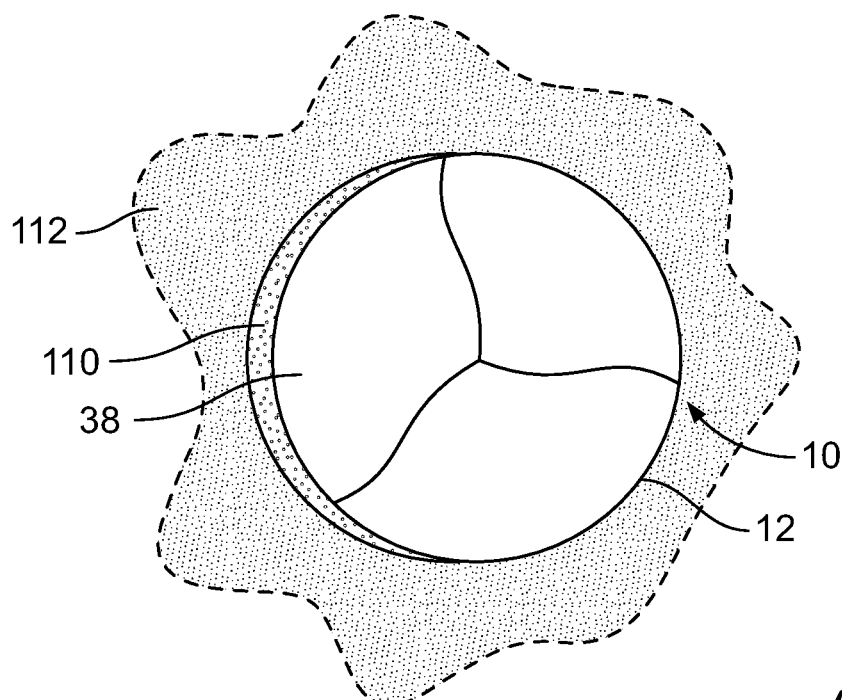
FIG. 4 is a highly schematic cross-section of the collapsible prosthetic heart valve of FIG. 1 mispositioned within the aortic valve annulus of a patient.

FIG. 4 is a highly schematic cross-section of prosthetic heart valve 10 mispositioned within the native aortic annulus of a patient. Mispositioning may occur as a result of delivery device 100 being misaligned with respect to the native aortic annulus when prosthetic heart valve 10 is deployed, or as a result of the prosthetic heart valve becoming repositioned as the valve contacts tissue. As seen in FIG. 4, a gap 110 may be formed between mispositioned prosthetic heart valve 10 and native valve annulus 112. Gap 110 may result in paravalvular leakage, enabling blood to flow through the gap from the aorta into the left ventricle during systole. Such leakage may reduce cardiac efficiency and increase strain on the heart muscle.

Figure 5:
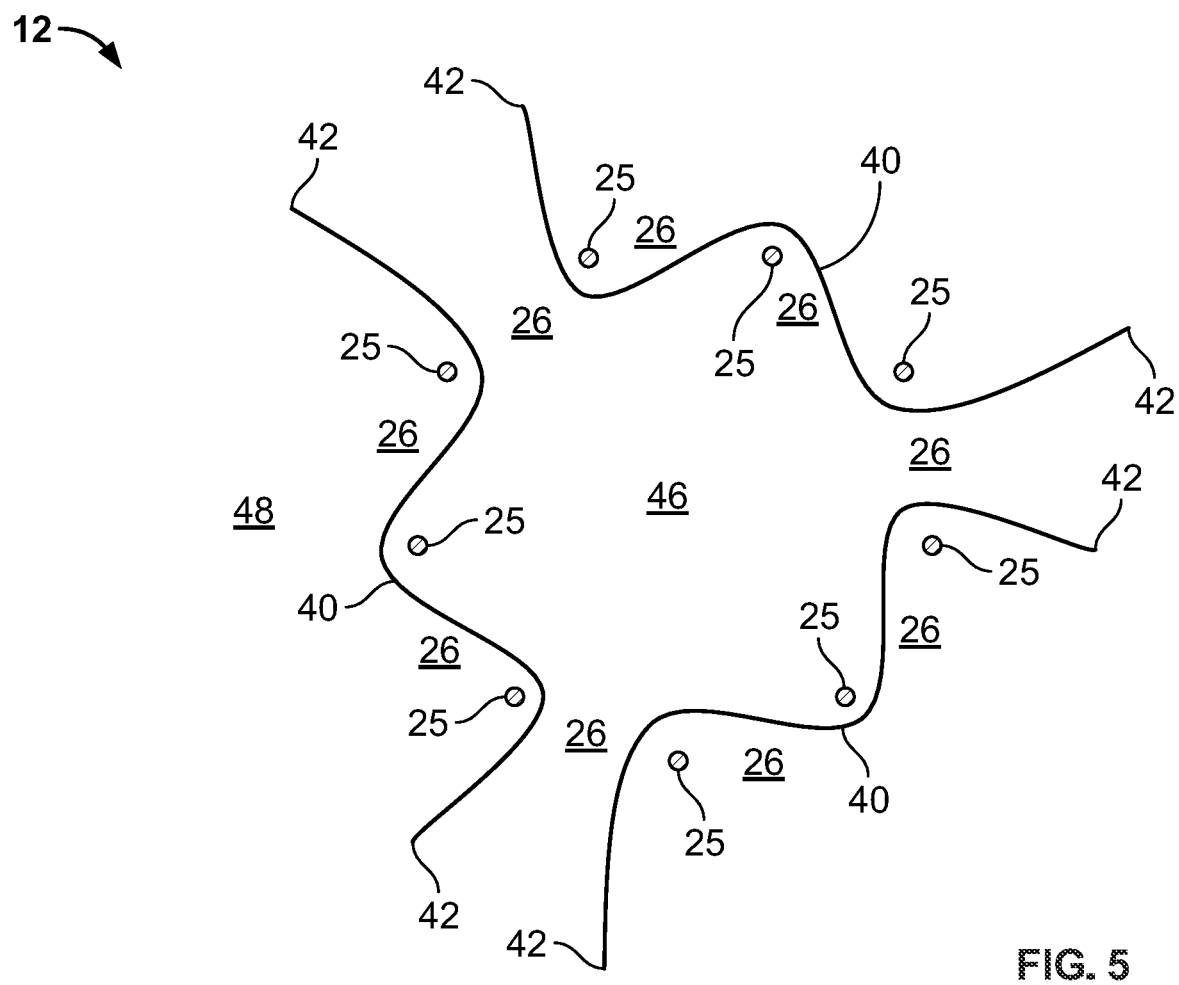
FIG. 5 is a transverse cross-section of the stent of the prosthetic heart valve of FIG. 1, showing the attachment of sutures to the stent.

Withdrawal of prosthetic heart valve 10 into distal sheath 102 after deployment requires at least partial collapsing of aortic end 16 from the expanded condition. Such collapsing may be accomplished by using one or more lengths of suture 40 threaded around struts 24 at junctures 25, as shown schematically in FIG. 5, to cinch aortic end 16 to a small enough diameter to reenter distal sheath 102. FIG. 5 is a transverse cross-section of stent 12 along section line 5-5 of FIG. 1. Section line 5-5 is the plane at which adjacent cells 26 in the row of cells at the aortic end 16 abut one another circumferentially and at which pairs of struts 24 meet each other to form junctures 25.

In the arrangement shown in FIG. 5, three lengths of suture 40 are threaded into stent 12, but more or fewer lengths of suture 40 may be used as appropriate for the size and configuration of stent 12. Suture 40 may be made of any biocompatible material having sufficient flexibility and tensile strength, such as nitinol. Further, suture 40 may be braided or monofilament. According to various arrangements, stent 40 may be threaded with only one length of suture 40, with a number of lengths of sutures 40 equal to a number of cells 26 in the row of cells at aortic end 16, or with any number of lengths of sutures 40 in between. The appropriate number of lengths of suture 40 may be greater for a larger stent 12 or a stent with more cells 26, and lesser for a smaller stent 12 or a stent with fewer cells 26. Further, the number of lengths of suture 40 may be varied to adjust the magnitude of force to be applied per length of suture 40 to collapse stent 12, as the magnitude of force per length of suture 40 necessary to contract or cinch stent 12 will generally be inversely proportional to the number of lengths of suture 40 threaded into stent 12. Thus, increasing the number of lengths of suture 40 threaded into stent 12 will accomplish either or both of distributing the force applied to each suture length across fewer struts 24 and increasing the number of suture lengths applying force to each strut 24. Each length of suture 40 is depicted in FIG. 5 as an individual suture 40, but in other arrangements a single suture 40 may be threaded through stent 12 multiple times. In arrangements in which multiple lengths of suture 40 are used, the multiple lengths of suture 40 may each have the same length or different lengths.

In the embodiment shown in FIG. 5, each length of suture 40 may be threaded into stent 12 by passing a first end of the length of suture through a first cell 26 from the abluminal side or exterior 48 of the stent into the lumen 46 of the stent. The first end of the length of suture 40 may then be passed around a first strut juncture 25 on the lumenal side of the stent 12 and outwardly to the exterior 48 of the stent through an adjacent cell 26. Subsequently, the length of suture 40 may be guided on the abluminal side 48 of a second strut juncture 25 circumferentially adjacent to the first strut juncture 25 and then back into the lumen 46 through a cell 26 on the side of the second strut juncture opposite the first strut juncture. The first end of the length of suture 40 may then be passed on the lumenal side of a third strut juncture 25 on the side of the second strut juncture opposite the first strut juncture, and through the next adjacent cell 26 to the exterior 48 of the stent. Thus, a single length of suture 40 may be threaded to pass around the lumenal side of two circumferentially spaced junctures 25, and around the abluminal side of one juncture 25 between the two circumferentially spaced junctures as illustrated in FIG. 5. However, it should be understood that in other arrangements, a single length of suture 40 may be threaded to pass around the abluminal side of multiple junctures 25 between the two circumferentially spaced junctures around which the suture 40 passes on the lumenal side.

Each length of suture 40 may be threaded partially into the lumen 46 of stent 12 and has two ends 42 that may extend from the abluminal side 48 of stent 12 and prosthetic heart valve 10 proximally through distal sheath 102 and the remainder of delivery device 100 for manipulation by a surgeon. In the example illustrated in FIG. 5, each length of suture 40 is threaded into stent 12 so as to extend circumferentially around the stent outside of junctures 25, except that each length of suture 40 is looped inside two circumferentially spaced junctures 25.

Figure 6:
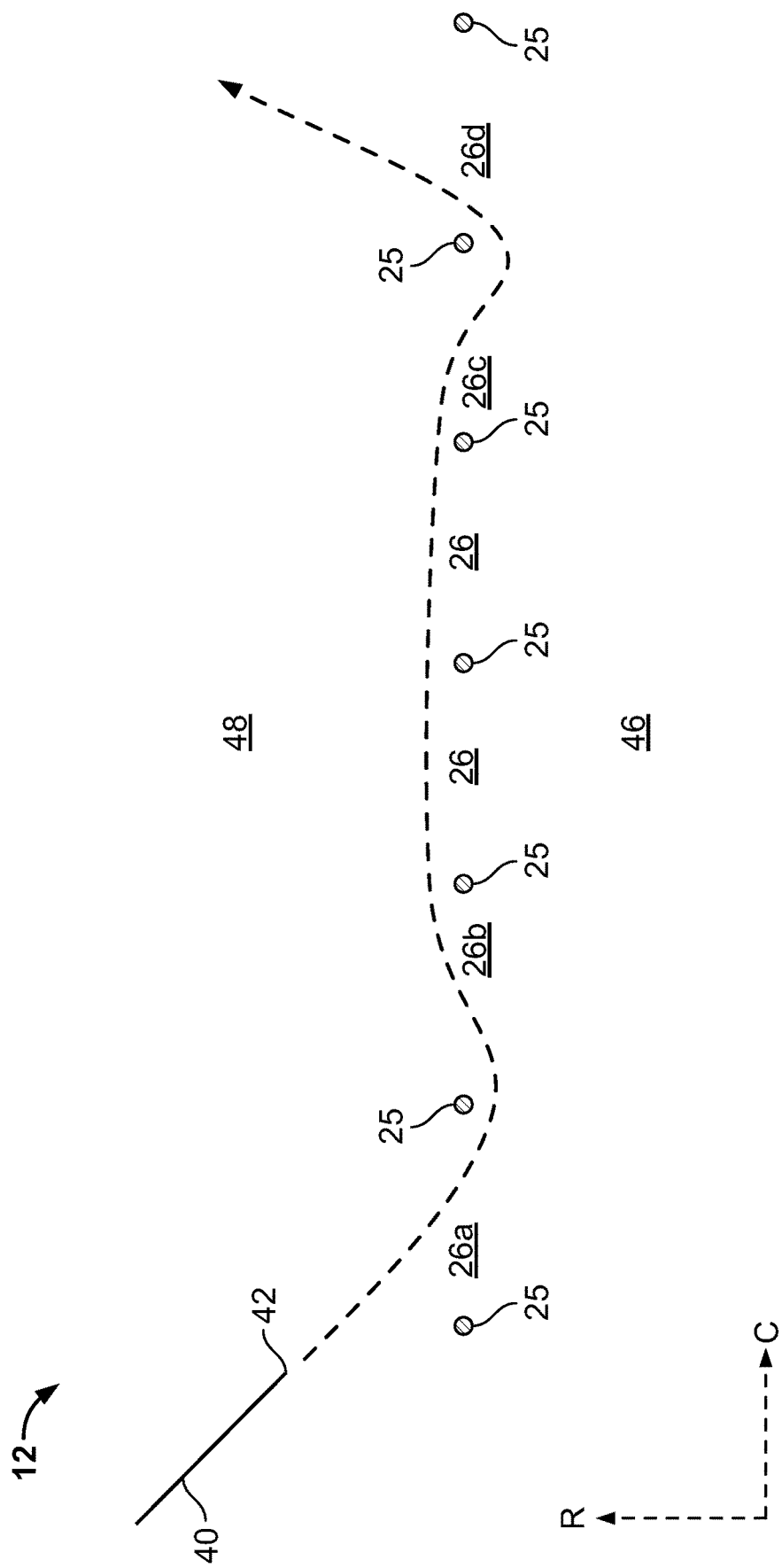
FIG. 6 is a partial transverse cross-section of the stent of the prosthetic heart valve of FIG. 1, showing the attachment of sutures to the stent according to another embodiment.

FIG. 6 illustrates with more detail an exemplary method for threading suture 40 into stent 12 according to another arrangement, though any method for threading suture 40 that makes cinching aortic end 16 possible by applying tension to ends 42 would be suitable. FIG. 6 depicts a portion of stent 12 as if stent 12 has an infinite diameter such that a circumferential direction C relative to stent 12 is a straight line. However, the method applies to a stent 12 having an oval or circular shape, as illustrated in FIGS. 1 and 5. Further, though only one length of suture 40 is illustrated in FIG. 6, this method may be used for each of any number of lengths of suture 40 that may be threaded into stent 12. A radial direction R extends perpendicular to circumferential direction C away from the center of stent 12.

The method of FIG. 6 may include passing a first end 42 of length of suture 40 radially inward from the abluminal side 48 of stent 12 through a first cell 26a into the lumen 46 of the stent, then looping the first end around a single strut juncture 25 and pulling the first end 42 radially outward to the abluminal side 48 of the stent through a second cell 26b circumferentially adjacent to the first cell. First end 42 may then be pulled in the circumferential direction C past one or more strut junctures 25 before being passed radially inward through a third cell 26c. For example, as illustrated in FIG. 6, end 42 may pass on the abluminal side 48 of three strut junctures 25 and two cells 26 between second cell 26b and third cell 26c. However, the length of suture 40 may pass on the abluminal side 48 of a greater or fewer number of strut junctures 25 and cells 26 between the two locations at which the length of suture 40 passes into the lumen 46 of stent 12. Finally, end 42 may be guided radially outward to the abluminal side 48 of the stent through a fourth cell 26d adjacent to the second cell 26c in the circumferential direction C.

Figure 7:
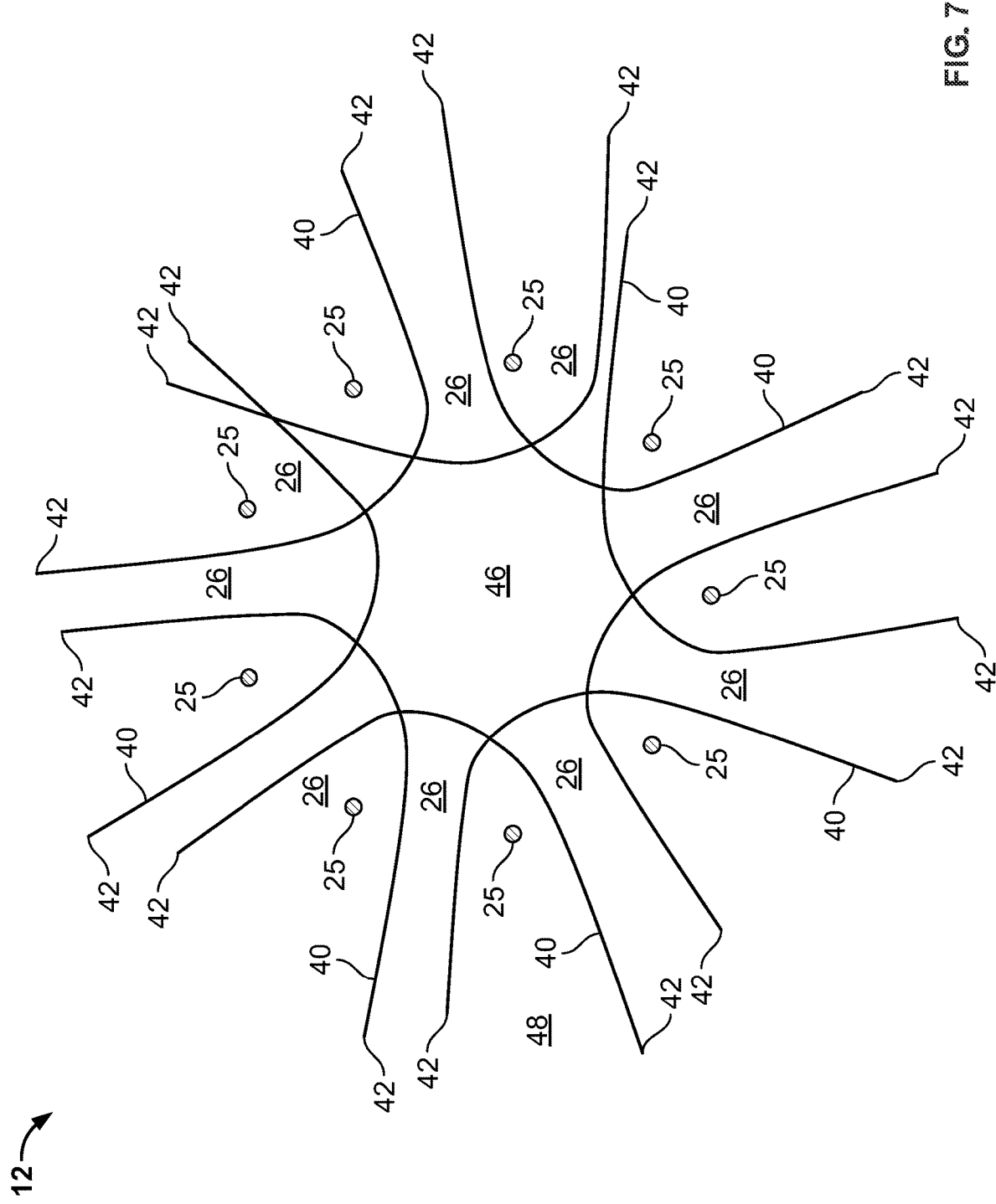
FIG. 7 is a transverse cross-section of the stent of the prosthetic heart valve of FIG. 1, showing the attachment of sutures to the stent according to another arrangement.

FIG. 7 is a transverse cross-section of stent 12 along section line 5-5 of FIG. 1, with lengths of suture 40 threaded according to another arrangement. Each length of suture 40 may be threaded into stent 12 so as to pass on the lumenal side of two junctures 25 and one cell 26 in the row of cells at aortic end 16. The number of lengths of suture 40 threaded into stent 12 may be equal to the number of cells 26 in the row of cells at aortic end 16, or the number of cells on the plane corresponding to section line 5-5, so that a single end 42 of two different lengths of suture 40 (two ends in total) extend outside of stent 12 from each cell 26 in the row of cells at aortic end 16.

Figure 8A:
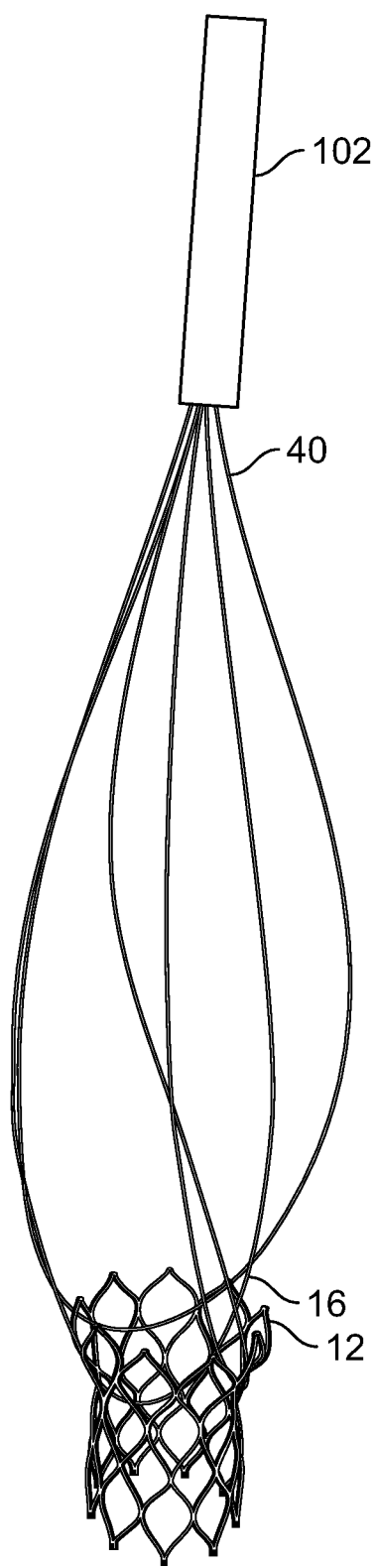
FIGS. 8A and 8B illustrates the collapsible prosthetic heart valve of FIG. 1 with the sutures of FIG. 5 extending into the delivery device of FIG. 3.
Figure 8B:
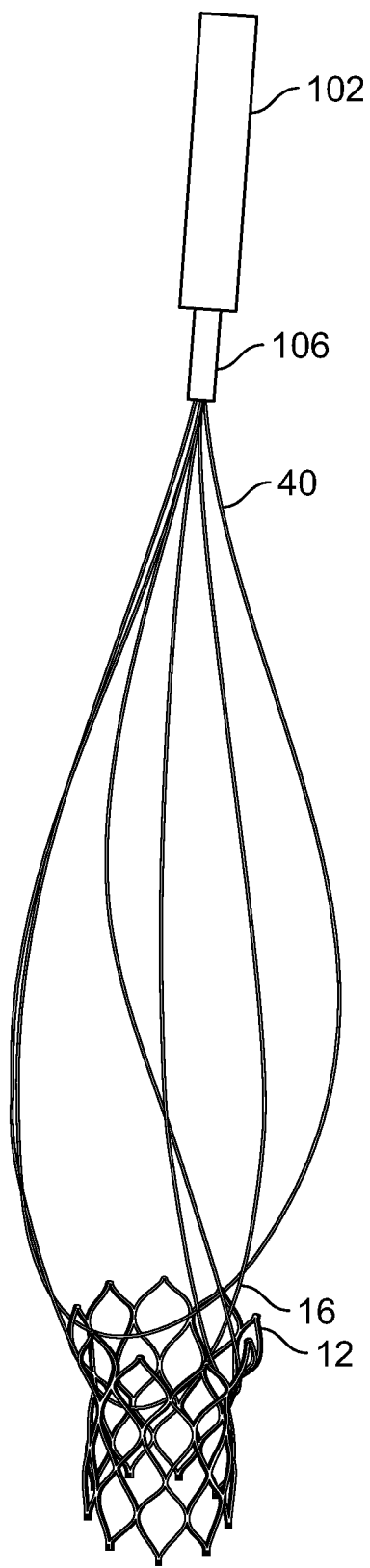

When sutures 40 are threaded as described with regard to any arrangement above, tension applied to the sutures by pulling ends 42 away from stent 12 cinches aortic end 16 by causing cell struts 24 to move toward one another in the circumferential direction C, collapsing the cells 26 at the aortic end so that they contract radially inward. Because sutures 40 extend from stent 12 into distal sheath 102 as shown in FIG. 8, tension on sutures 40 will generally be applied both radially inward relative to stent 12 and in an axial direction toward the delivery device and its user. Such tension reduces the length of the sutures 40 between strut junctures 25 around which the sutures are looped, drawing the corresponding struts 24 radially inward toward one another and contracting aortic end 16 to a smaller diameter. In arrangements in which lengths of suture 40 are threaded to extend around the abluminal side 48 of junctures 25, such as those illustrated in FIGS. 5 and 6, the tension on the lengths of suture causes the suture to apply radially inward pressure against the junctures, resulting in contraction of the stent 12. In arrangements in which the lengths of suture 40 are threaded to extend into and out from the lumen 46 without passing radially across the abluminal side 48 of any junctures 25, such as the arrangement shown in FIG. 7, drawing the lengths of suture into the relatively narrow sheath 102 causes proximal ends of the struts 24 around which the sutures are looped to be pulled inward toward the center of the sheath along with the sutures. Contraction resulting from the creation of tension in sutures 40 is illustrated in progressive stages by FIGS. 9A-9C. Upon contraction of aortic end 16 to a suitably narrow diameter, valve 10 may be withdrawn partially or entirely into distal sheath 102. Such withdrawal enables a surgeon to easily withdraw valve 10 from the patient and to reattempt delivery of valve 10 as many times as necessary, even after valve 10 has fully exited distal sheath 102. The option to contract and withdraw a fully deployed valve 10 permits assessment of the position and performance of valve 10 in substantially the final state of installation. That is, the surgeon may deploy valve 10 such that valve 10 exits distal sheath 102 entirely, reaches the fully expanded condition, and seats into native aortic valve AV in an intended permanent location before assessing the valve's placement. If the placement of valve 10 is found to be unsatisfactory, the surgeon may apply tension to the ends 42 of sutures 40 to cinch the aortic end 16 of stent 12, then withdraw valve 10 into distal sheath 102 and reattempt deployment as necessary. If the placement of valve 10 is found to be satisfactory, the surgeon may remove sutures 40 from the valve by releasing one end 42 of each suture while retaining the other ends 42, then pulling the retained ends 42 until sutures 40 are removed from stent 12 and, eventually, the patient.

To summarize the foregoing, disclosed is a heart prosthesis system, including a prosthetic heart valve, the prosthetic heart valve including a collapsible and expandable stent having an aortic end, an annulus end, and a plurality of openings arranged circumferentially around the aortic end, the aortic end having a first diameter in an expanded condition, and a valve assembly mounted within the stent; and a length of suture threaded through the openings such that tension applied to the length of suture in a direction away from the stent will collapse the aortic end of the stent from a first diameter to a second diameter less than the first diameter; and/or the length of suture may be threaded through the openings so as to extend in a circumferential direction around a portion of the aortic end of the stent; and/or the stent may include struts which form circumferentially extending rows of cells, each cell defining one of the openings; and/or the length of suture may pass through a first one and a second one of the cells in a first row, and through a third one and a fourth one of the cells in the first row; and/or the length of suture may pass through only the first, second, third, and fourth ones of the cells; and/or the first and second ones of the cells may be circumferentially adjacent to one another and the third and fourth ones of the cells may be circumferentially adjacent to one another; and/or the length of suture may include a plurality of lengths of suture, and two of the length of suture may extend through one of the openings; and/or the system may further includes a sheath for delivering the heart valve into the heart of a patient.

Also disclosed is a method of deploying a prosthetic heart valve into the heart of a patient, the method including inserting a delivery sheath into the heart of the patient, the delivery sheath holding the prosthetic heart valve in a collapsed condition therein; deploying the prosthetic heart valve into the heart, the prosthetic heart valve including a collapsible and expandable stent, a valve assembly mounted within the stent, the stent having an aortic end, an annulus end, a plurality of openings arranged circumferentially around the aortic end, and a length of suture threaded through a group of the openings and through the delivery sheath, the deployed heart valve having a first diameter; applying tension to ends of the length of suture, whereupon the length of suture collapses the aortic end of the stent from the first diameter to a second diameter less than the first diameter; and withdrawing the collapsed aortic end of the stent at least partially into the delivery sheath; and/or the deploying step may cause the aortic end and the annulus end of the stent to exit the delivery sheath; and/or the deploying step may cause the aortic end of the stent to expand from the collapsed condition to an expanded condition; and/or the withdrawing step may be accomplished by applying additional tension to the ends of the length of suture; and/or the method may further include redeploying the prosthetic heart valve into the heart of the patient after the withdrawing step; and/or the length of suture may have a first end and a second end and the method may further include removing the length of suture from the deployed heart valve by releasing the first end of the length of suture and pulling the second end of the length of suture until the first end exits the deployed heart valve; and/or the method may further include assessing the position of the heart valve after the deploying step; and/or the step of applying tension to the length of suture may include applying tension to a plurality of lengths of suture, each of the plurality of lengths of suture being threaded through a different group of the openings; and/or the stent may include a circumferential row of nine openings and the plurality of lengths of suture may be three sutures each extending through four openings of the row of nine openings.

Also disclosed is a heart prosthesis system including a prosthetic heart valve, the prosthetic heart valve including a collapsible and expandable stent having an aortic end, an annulus end, and a plurality of struts defining a plurality of cells, the cells being arranged in multiple circumferentially extending rows, the aortic end having a first diameter in an expanded condition of the stent; and a valve assembly mounted within the stent, and the system further including a length of suture threaded through the cells so as to extend in a circumferential direction around a portion of the aortic end of the stent, whereby tension applied to the length of suture in a direction away from the stent will collapse the aortic end of the stent from the first diameter to a second diameter less than the first diameter.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A heart prosthesis system, comprising:
a prosthetic heart valve, comprising:
a collapsible and expandable stent having an aortic end, an annulus end, and a plurality of struts defining complete cells arranged circumferentially around the aortic end, each complete cell having a cell opening fully surrounded by ones of the struts, the aortic end having a first diameter in an expanded condition; and
a valve assembly mounted within the stent; and
a length of suture threaded through only the cell openings, the length of suture passing from an exterior of the stent to an interior of the stent through one of the cell openings and then passing from the interior of the stent to the exterior of the stent through another one of the cell openings such that the length of suture passes only once through each of the cell openings, the length of suture having a pair of free ends that extend away from the stent, the length of suture having a sufficient length that the free ends are located outside of a patient when the prosthetic heart valve is at least partially expanded within the patient, whereby tension applied to the free ends of the length of suture in a direction away from the stent will cause the length of suture to slide within the cell openings and collapse the aortic end of the stent from the first diameter to a second diameter less than the first diameter.

2. The system of claim 1, wherein the length of suture is threaded through the cell openings so as to extend in a circumferential direction around a portion of the aortic end of the stent.

3. The system of claim 2, wherein the length of suture passes through a first one and a second one of the cell openings in a first row, and through a third one and a fourth one of the cell openings in the first row.

4. The system of claim 3, wherein the length of suture passes through only the first, second, third, and fourth ones of the cell openings.

5. The system of claim 3, wherein the first and second ones of the cell openings are circumferentially adjacent to one another and the third and the fourth ones of the cell openings are circumferentially adjacent to one another.

6. The system of claim 1, further comprising additional lengths of suture, wherein two of the additional lengths of suture extend through one of the cell openings.

7. The system of claim 1, further comprising a sheath for delivering the heart valve into the heart of a patient.

8. A heart prosthesis system, comprising:
a prosthetic heart valve, comprising:
a collapsible and expandable stent having an aortic end, an annulus end, and a plurality of struts defining a plurality of complete cells, the complete cells being arranged in multiple circumferentially extending rows, each complete cell having a cell opening fully surrounded by ones of the struts, the aortic end having a first diameter in an expanded condition of the stent; and
a valve assembly mounted within the stent; and
a length of suture threaded through only the cell openings so as to extend in a circumferential direction around a portion of the aortic end of the stent, the length of suture passing from an exterior of the stent to an interior of the stent through one of the cell openings and then passing from the interior of the stent to the exterior of the stent through another one of the cell openings such that the length of suture passes only once through each of the cell openings, the length of suture having a pair of free ends that extend away from the stent, the length of suture having a sufficient length that the free ends are located outside of a patient when the prosthetic heart valve is at least partially expanded within the patient, whereby tension applied to the free ends of the length of suture in a direction away from the stent will cause the length of suture to slide within the cell openings and collapse the aortic end of the stent from the first diameter to a second diameter less than the first diameter.

* * * * *